United States Patent
Tong et al.

(10) Patent No.: US 8,709,388 B2
(45) Date of Patent: Apr. 29, 2014

(54) COSMETIC COMPOSITION BASED ON A SUPRAMOLECULAR POLYMER AND A HYPERBRANCHED FUNCTIONAL POLYMER

(75) Inventors: Anita Chon Tong, Westfield, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/418,145

(22) Filed: Mar. 12, 2012

(65) Prior Publication Data

US 2013/0236407 A1    Sep. 12, 2013

(51) Int. Cl.
*A61K 8/00*    (2006.01)

(52) U.S. Cl.
USPC ............................................................ 424/64

(58) Field of Classification Search
None
See application file for complete search history.

(56) References Cited

U.S. PATENT DOCUMENTS

| | | | |
|---|---|---|---|
| 7,862,805 B2 | 1/2011 | Mougin et al. | |
| 7,951,207 B2 | 5/2011 | Brun et al. | |
| 2003/0039621 A1 | 2/2003 | Arnaud et al. | |
| 2004/0096470 A1 | 5/2004 | Tanaka et al. | |
| 2007/0189991 A1 | 8/2007 | Mougin et al. | |
| 2007/0264208 A1 | 11/2007 | Mougin et al. | |
| 2010/0028277 A1 | 2/2010 | Chodorowski-Kimmes et al. | |
| 2010/0158832 A1 | 6/2010 | Chodorowski-Kimmes et al. | |
| 2010/0239509 A1 | 9/2010 | Chodorowski-Kimmes et al. | |
| 2010/0242188 A1 | 9/2010 | Daubresse et al. | |
| 2010/0247466 A1 | 9/2010 | Mougin et al. | |
| 2010/0278764 A1 | 11/2010 | Mougin et al. | |
| 2011/0094531 A1 | 4/2011 | Abbas | |
| 2011/0189118 A1 | 8/2011 | Mougin et al. | |
| 2011/0200547 A1 | 8/2011 | Mougin et al. | |

FOREIGN PATENT DOCUMENTS

| | | |
|---|---|---|
| FR | 2954132 A1 | 6/2011 |
| FR | 2956317 A1 | 8/2011 |
| FR | 2961102 A1 | 12/2011 |
| WO | WO-2011073294 A1 | 6/2011 |
| WO | WO-2011073295 A1 | 6/2011 |
| WO | WO 2011080043 A1 * | 7/2011 |
| WO | WO-2011080043 A1 | 7/2011 |
| WO | WO-2011080448 A2 | 7/2011 |
| WO | WO-2011080450 A1 | 7/2011 |
| WO | WO-2011080494 A2 | 7/2011 |
| WO | WO-2011083240 A1 | 7/2011 |
| WO | WO-2011083243 A1 | 7/2011 |
| WO | WO-2011147696 A1 | 12/2011 |
| WO | WO-2011147697 A1 | 12/2011 |
| WO | WO-2011148323 A1 | 12/2011 |
| WO | WO-2011148324 A2 | 12/2011 |
| WO | WO-2011148325 A1 | 12/2011 |
| WO | WO-2011148327 A1 | 12/2011 |
| WO | WO-2011148328 A2 | 12/2011 |
| WO | WO-2011151776 A1 | 12/2011 |

OTHER PUBLICATIONS

Baker Hughes, Performa V 6112 Polymer, Specialty polymers and waxes to meet your needs, available Mar. 2012.*
Tom F.A. de Greef et al., "Supramolecular polymers," Nature, vol. 453/8, pp. 171-173, May 2008.
English Abstract of FR-2961102-A1, Dec. 16, 2001.
English Abstract of FR-2954132-A1, Jun. 24, 2011.
English Abstract of FR-2956317-A1, Aug. 19, 2011.

* cited by examiner

*Primary Examiner* — Anand Desai
*Assistant Examiner* — Melissa Mercier
(74) *Attorney, Agent, or Firm* — Novak Druce Connolly Bove + Quigg LLP

(57) ABSTRACT

The present invention relates to a cosmetic composition and method for making up and/or enhancing the appearance of a keratinous substrate, comprising at least one supramolecular polymer, at least one detackifying ingredient which is a hyperbranched functional polymer and at least one fatty phase ingredient(s). The compositions of the present invention may optionally contain at least one wax and at least one colorant.

33 Claims, No Drawings

COSMETIC COMPOSITION BASED ON A SUPRAMOLECULAR POLYMER AND A HYPERBRANCHED FUNCTIONAL POLYMER

FIELD OF THE INVENTION

The present invention relates to a cosmetic composition and method for making up and/or enhancing the appearance of a keratinous substrate, comprising at least one supramolecular polymer, at least one detackifying ingredient which is a hyperbranched functional polymer and at least one fatty phase ingredient(s). The compositions of the present invention may optionally contain at least one wax and at least one colorant.

DISCUSSION OF THE BACKGROUND

In general, when women use a makeup product, especially a foundation or lipstick, they wish this product to have good wear and transfer resistance properties.

With regard to this expectation, one or more polymers are typically employed to improve these properties. Illustrations of these polymers include silicone resins, polyacrylates and latices.

However, the above-mentioned polymers, which are advantageous in terms of wear and transfer-resistance properties, are often found by consumers to be uncomfortable with regards to their initial application (difficult to spread and tacky feeling) and/or after application (tautness, mask effect). In addition, silicone resins provide no shine and moisture to the lip.

Supramolecular polymers such as those described in patent applications EP 2 189 151 and FR 2 938 758 are known for their good wear properties. There remains, however, a sensation of "tackiness" experienced by the user during and after their application on the skin and/or the lips.

Unexpectedly, the inventors have found that it is possible to overcome this drawback by combining certain supramolecular polymers with a hyperbranched functional polymer. In addition, the inventive compositions demonstrate significantly reduced tack. At the same time, the inventive compositions provided an even film deposit, a good comfort level, and more moisture on the wearer's lips.

SUMMARY OF THE INVENTION

The object of the present invention is to provide a cosmetic composition for making up and/or enhancing the appearance of keratinous substrates containing, in a cosmetically acceptable medium:
a) at least one supramolecular polymer,
b) at least one detackifying ingredient which is a hyperbranched functional polymer,
c) at least one fatty phase;
d) optionally, at least one wax; and
e) optionally, at least one colorant,
wherein the supramolecular polymer is based on functionalized polyalkene polymer of formula HO—P—OH in which P represents a homopolymer or a copolymer that may be obtained by polymerization of one or more linear or cyclic polyunsaturated $C_2$-$C_{10}$ and preferably $C_2$-$C_4$ alkenes, further wherein said one or more linear or cyclic polyunsaturated $C_2$-$C_{10}$ alkenes may be branched, further wherein said supramolecular polymer may be derived from the reaction, especially the condensation, of said functionalized polyalkene polymer with at least one junction group functionalized with at least one reactive group capable of reacting with the reactive group(s) of the functionalized polyalkene polymer, the said junction group being capable of forming at least 3 hydrogen bonds, preferably at least 4 hydrogen bonds, preferentially 4 hydrogen bonds, and wherein the composition provides good wear of color without tackiness on the lips.

According to another aspect of the present invention, there is provided a method of making up and/or enhancing the appearance of a keratinous substrate involving or comprising applying onto the keratinous substrate the above-disclosed composition, wherein the composition provides good wear of color without tackiness on the lips.

DESCRIPTION OF THE INVENTION

Other than in the operating examples, or where otherwise indicated, all numbers expressing quantities of ingredients and/or reaction conditions are to be understood as being modified in all instances by the term "about" which encompasses ±10%.

"Keratinous substrate" may be chosen from, for example, hair, eyelashes, lip, and eyebrows, as well as the stratum corneum of the skin and nails.

"Polymers" as defined herein, include homopolymers and copolymers formed from at least two different types of monomers.

As used herein, the expression "at least one" means one or more and thus includes individual components as well as mixture/combinations.

The "wear" of compositions as used herein, refers to the extent by which the color of the composition remains the same or substantially the same as at the time of application, as viewed by the naked eye, after a certain period or an extended period of time. Wear properties may be evaluated by any method known in the art for evaluating such properties. For example, wear may be evaluated by a test involving the application of a composition to human hair, skin or lips and evaluating the color of the composition after a specified period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between, the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

Supramolecular Polymer

The composition according to the invention comprises at least one supramolecular polymer comprising a polyalkene-based supramolecular polymer. In particular; the polyalkene-based supramolecular polymer is obtained by a reaction, especially the condensation, of at least one polyalkene polymer functionalized with at least one reactive group, with at least one junction group functionalized with at least one reactive group capable of reacting with the reactive group(s) of the functionalized polyalkene polymer, said junction group being capable of forming at least three hydrogen bonds and preferably at least four hydrogen bonds, preferentially four hydrogen bonds.

The terms "polyalkene" and "polyolefin" mean a polymer derived from the polymerization of at least one monomer of alkene type, comprising an ethylenic unsaturation, the said monomer possibly being pendent or in the main chain of the said polymer. The terms "polyalkene" and "polyolefin" are thus directed towards polymers that may or may not comprise a double bond. Preferably, the supramolecular polymers used according to the invention are prepared from a polymer derived from the polymerization of an alkene comprising at least two ethylenic unsaturations.

The supramolecular polymer according to the invention is capable of forming a supramolecular polymer chain or network, by (self)assembly of said polymer according to the invention with at least one other identical or different polymer according to the invention, each assembly involving at least one pair of paired junction groups, which may be identical or different, borne by each of the polymers according to the invention.

For the purposes of the invention, the term "junction group" means any group comprising groups that donate or accept hydrogen bonds, and capable of forming at least three hydrogen bonds and preferably at least four hydrogen bonds, preferentially four hydrogen bonds, with an identical or different partner junction group. These junction groups may be lateral to the polymer backbone (side branching) and/or borne by the ends of the polymer backbone, and/or in the chain forming the polymer backbone. They may be distributed in a random or controlled manner.

Functionalized Polyalkene

The polyalkene polymers are functionalized with at least one reactive group and preferably with at least two reactive groups. The functionalization preferably occurs at the chain ends. They are then referred to as telechelic polymers.

The functionalization groups, or reactive groups, may be attached to the polyalkene polymer via linkers, preferably linear or branched $C_1$-$C_4$ alkylene groups, or directly via a single bond.

Preferably, the functionalized polyalkene polymers have a number-average molecular mass (Mn) of between 1000 and 8000.

Even more preferably, they have a number-average molecular mass of between 1000 and 5000, or even between 1500 and 4500.

Even more preferably, they have a number-average molecular mass of between 2000 and 4000.

Preferably, the functionalized polyalkene polymer, capable of forming all or part of the polymer backbone of the supramolecular polymer according to the invention (preferably, it forms all of the backbone of the polymer), is of formula HO—P—OH in which:

P represents a homo- or copolymer that may be obtained by polymerization of one or more linear, cyclic and/or branched, polyunsaturated (preferably diunsaturated) $C_2$-$C_{10}$ and preferably $C_2$-$C_4$ alkenes.

P preferably represents a homo- or copolymer that may be obtained by polymerization of one or more linear or branched, $C_2$-$C_4$ diunsaturated alkenes.

More preferably, P represents a polymer chosen from a polybutylene, a polybutadiene (such as a 1,4-polybutadiene or a 1,2-polybutadiene), a polyisoprene, a poly(1,3-pentadiene) and a polyisobutylene, and copolymers thereof.

According to one preferred embodiment, P represents a poly(ethylene/butylene) copolymer.

The preferred poly(ethylene/butylenes) are copolymers of 1-butene and of ethylene. They may be represented schematically by the following sequence of units: [—$CH_2$—$CH_2$—] and [—$CH_2CH(CH_2$—$CH_3$)—].

According to a second preferred embodiment, P is a polybutadiene homopolymer, preferably chosen from a 1,4-polybutadiene or a 1,2-polybutadiene. The polybutadienes may be 1,4-polybutadienes or 1,2-polybutadienes, which may be represented schematically, respectively, by the following sequences of units:

[—$CH_2$—CH=CH—$CH_2$—] (1,4-polybutadienes), [—$CH_2$—CH(CH=$CH_2$)—] (1,2-polybutadienes).

Preferably, they are 1,2-polybutadienes. Preferably, P is a 1,2-polybutadiene homopolymer. According to another embodiment, P is a polyisoprene. Polyisoprenes may be represented schematically by the following sequences of units:

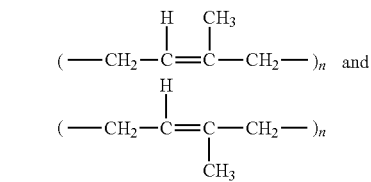

A mixture of above units may obviously also be used, so as to form copolymers.

The functionalized polyalkene polymers may be totally hydrogenated to avoid the risks of crosslinking. Preferably, the functionalized polyalkene polymers used in the compositions according to the invention are hydrogenated.

Preferably, the polyalkene polymers are hydrogenated and functionalized with at least two OH reactive groups, which are preferably at the ends of the polymers.

Preferably, they have functionality as hydroxyl end groups of from 1.8 to 3 and preferably in the region of 2.

The polydienes containing hydroxyl end groups are especially defined, for example, in FR 2 782 723. They may be chosen from polybutadiene, polyisoprene and poly(1,3-pentadiene) homopolymers and copolymers. Mention will be made in particular of the hydroxylated polybutadienes sold by the company Sartomer, for instance the Krasol® Resins and the Poly Bd® Resins. Preferably, they are hydrogenated dihydroxylated 1,2-polybutadiene homopolymers, such as Nisso-PB 1, GI3000, GI2000 and GI1000 sold by the company Nisso, which may be represented schematically by the following formula:

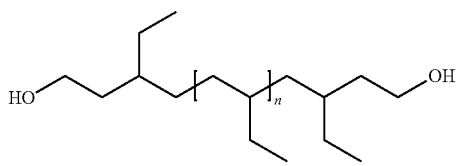

Preferably, n is between 14 and 105 and preferably between 20 and 85.

These polymers have the following number-average molecular masses: GI3000 of Mn=4700, GI2000 of Mn=3300 and GI1000 of Mn=1500. These values are measured by GPC according to the following protocol.

Protocol for Determining the Molecular Masses by GPC

Determination of the number-average molecular mass $\overline{M_n}$ the weight-average molecular mass $\overline{M_w}$ and the polydispersity index $\overline{M_w}/\overline{M_n}$ in polystyrene equivalents.

Preparation of the standard solutions

Prepared the polystyrene standards from Varian kits (ref.: PS-H (PL2010-0200)

The calibration masses are the following:

PS 6035000-PS 3053000-PS 915000-PS 483000-PS 184900-PS 60450-PS 19720-PS 8450-PS 3370-PS 1260-PS 580

Inject 100 µl of each of the solutions into the calibration column.

Preparation of the sample:

Prepare a solution with a solids content of 0.5% in THF (tetrahydrofuran).

Prepare the solution about 24 hours before injection. Filter the solution through a Millex FH filter (0.45 µm).

Inject into the column.

Chromatographic conditions:

Columns: PL Rapid M (batch 5M-Poly-008-15) from Polymer Labs

PL-gel HTS-D (batch 5M-MD-72-2) from Polymer Labs

PL-gel HTS-F (10M-2-169B-25) from Polymer Labs

PL-Rapid-F (6M-0L1-011-6) from Polymer Labs

Length: 150 mm-inside diameter: 7.5 mm

Pump: isocratic M1515 Waters

Eluent: THF

Flow rate: 1 ml/minute

Temperature: ambient

Injection: 100 µl at 0.5% AM (active material) in the eluent

Detection: RI 64 mV (Waters 2424 refractometer)

Temperature: 45° C.

UV at 254 nm at 0.1 OD (Waters 2487 UV detector)

Integrator: Empower option GPC

Determination of the molar masses

The average molar masses are determined by plotting the calibration curve: Log molar mass=f (illusion volume at the top of the RI detection peak) and using the Empower option GPC software from Waters.

Among the polyolefins with hydroxyl end groups, mention may be made preferentially of polyolefins, homopolymers or copolymers with α,ω-hydroxyl end groups, such as polyisobutylenes with α,ω-hydroxyl end groups; and the copolymers of formula:

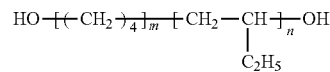

where (m+n) is from 1 to 100 and 0<n<(m+n), more preferably (m+n) is from 5 to 50 and 0<n<(m+n); most preferably (m+n) is from 9 to 35 and 0<n<(m+n).

In a preferred embodiment, the copolymers of the above formula are those sold by Mitsubishi under the brand name Polytail.

Junction Group

The supramolecular polymers according to the invention also have in their structure at least one residue of a junction group capable of forming at least three hydrogen bonds and preferably at least four hydrogen bonds, said junction group being initially functionalized with at least one reactive group.

Unless otherwise mentioned, the term "junction group" means in the present description the group without its reactive function.

The reactive groups are attached to the junction group via linkers L.

L is a single bond or a saturated or unsaturated $C_1$-$C_{20}$ divalent carbon-based group chosen in particular from a linear or branched $C_1$-$C_{20}$ alkylene; a $C_5$-$C_{20}$ (alkyl)cycloalkylene alkylene (preferably cyclohexylene methylene), a $C_{11}$-$C_{20}$ alkylene-biscycloalkylene (preferably alkylene-biscyclohexylene), a $C_6$-$C_{20}$ (alkyl)arylene, and an alkylene-bisarylene (preferably an alkylene-biphenylene); the linker L possibly being substituted with at least one alkyl group and/or possibly comprising 1 to 4 N and/or O heteroatoms, especially in the form of an $NO_2$ substituent.

Preferably, the linker is a group chosen from phenylene; 1,4-nitrophenylene; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylene bis(cyclohexylene); tolylene; 2-methyl-1,3-phenylene; 4-methyl-1,3-phenylene; and 4,4-biphenylenemethylene.

Preferably, the linker is chosen from the groups:

$C_5$-$C_{20}$ (alkyl)cycloalkylene alkylene, such as isophorone, $C_{11}$-$C_{25}$ alkylene-biscycloalkylene, such as 4,4'-methylene biscyclohexene, $C_1$-$C_{20}$ alkylene such as —$(CH_2)_2$—; —$(CH_2)_6$—; —$CH_2CH(CH_3)$—$CH_2$—$C(CH_3)_2$—$CH_2$—$CH_2$—, and $C_6$-$C_{20}$ (alkyl) phenylene, such as 2-methyl-1,3-phenylene.

Preferably, L is chosen from: -isophorone-; —$(CH_2)_2$—; —$(CH_2)_6$—; —$CH_2CH(CH_3)$—$CH_2$—$C(CH_3)_2$—$CH_2$—$CH_2$—; 4,4'-methylene biscyclohexylene; and 2-methyl-1,3-phenylene.

According to one particularly preferred embodiment, the linker is an alkylcycloalkylene alkylene.

Preferably, according to this embodiment, the linker is an isophorone group. The term "isophorone" means the following group:

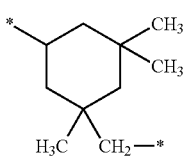

where each * represents a reactive group.

The said reactive groups functionalizing the junction group must be capable of reacting with the —OH reactive group(s) borne by the functionalized polyalkene.

Reactive groups that may be mentioned include isocyanate (—N=C=O) and thioisocyanate (—N=C=S) groups. Preferably, it is a group —N=C=O (isocyanate).

The functionalized junction groups capable of forming at least three H bonds may comprise at least three identical or different functional groups, and preferably at least four functional groups, chosen from:

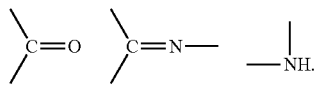

These functional groups may be classified into two categories:

functional groups that donate H bonds:

functional groups that accept H bonds:

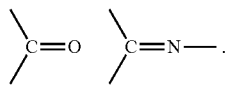

The junction groups capable of forming at least three hydrogen bonds form a basic structural element comprising at least three groups, preferably at least four groups and more preferentially four functional groups capable of establishing hydrogen bonds. Said basic structural elements capable of establishing hydrogen bonds may be represented schematically in the following manner:

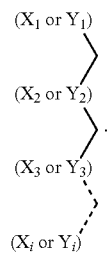

in which each of $X_1$ to $X_i$ is an hydrogen-bond accepting functional group (identical or different) and each of $Y_1$ to $Y_i$ is an hydrogen-bond donating functional group (identical or different).

Thus, each structural element should be able to establish hydrogen bonds with one or more partner structural elements, which are identical (i.e. self-complementary) or different, such that each pairing of two partner structural elements takes place by formation of at least three hydrogen bonds, preferably at least four hydrogen bonds and more preferentially four hydrogen bonds.

A proton acceptor X will pair with a proton donor Y. Several possibilities are thus offered, for example pairing of:

XXXX with YYYY;
XXXY with YYYX;
XXYX with YYXY;
XYYX with YXXY;
XXYY with YYXX self-complementary or otherwise;
XYXY with YXYX self-complementary or otherwise.

Preferably, the junction groups may establish four hydrogen bonds with an identical (or self-complementary) partner group among which are two donor bonds (for example

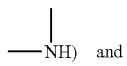

two acceptor bonds
(for example

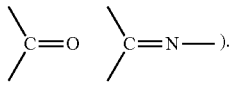

Preferably, the junction groups capable of forming at least four hydrogen bonds are chosen from:
ureidopyrimidones of formula (capable of forming at least four hydrogen bonds):

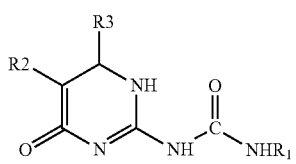

it being understood that all the tautomeric forms are included.

In this formula, $R_1$, $R_2$ and $R_3$ have the following meanings:

$R_1$ (or $R_1$ and $R_2$) are single bonds constituting the point of attachment of the junction group to the linker capable of forming at least three (preferably four) hydrogen bonds to the rest of the graft. Preferably, the said point of attachment is borne solely by $R_1$, which is a single bond.

$R_2$ represents a single bond or a divalent group chosen from a $C_1$-$C_6$ alkylene or a monovalent group chosen from a hydrogen atom, or a linear or branched, saturated $C_1$-$C_{10}$ monovalent hydrocarbon-based group, which may contain one or more heteroatoms such as O, S or N, these groups being optionally substituted with a hydroxyl, amino and/or thio group.

Preferably, $R_2$ may be a single bond or a monovalent group chosen from H, $CH_2OH$, $(CH_2)_2$—OH and $CH_3$.

According to one particularly preferred embodiment, $R_2$ is H.

$R_3$ represents a monovalent or divalent group, in particular, $R_3$ is chosen from a hydrogen atom or a linear or branched $C_1$-$C_{10}$ saturated monovalent hydrocarbon-based group, which may contain one or more heteroatoms such as O, S or N, these groups being optionally substituted with a hydroxyl, amino and/or thio function.

Preferably, $R_3$ may be a monovalent group chosen from H, $CH_2OH$, $(CH_2)_2$—OH and $CH_3$.

According to one particularly preferred embodiment, $R_3$ is a methyl group.

According to one preferred embodiment, the junction groups are chosen from 2-ureidopyrimidone and 6-methyl-2-ureidopyrimidone. Preferably, the preferred junction group is 6-methyl-2-ureidopyrimidone.

The junction groups, and especially the ureidopyrimidone junction groups, may be added directly or may be formed in situ during the process for preparing the supramolecular polymer. The first and second preparation methods described below illustrate these two alternatives, respectively.

In particular, the functionalized junction groups capable of reacting with the functionalized polyalkene polymer to give the supramolecular polymer according to the invention are preferably of formula:

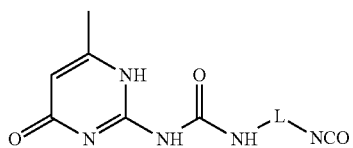

in which L is as defined above.

Preferably, L is chosen from the groups:

$C_5$-$C_{20}$ (alkyl)cycloalkylene alkylene, such as isophorone, $C_{11}$-$C_{25}$ alkylene-biscycloalkylene, such as 4,4'-methylene biscyclohexene, $C_1$-$C_{20}$ alkylene such as —$(CH_2)_2$—; —$(CH_2)_6$—; —$CH_2CH(CH_3)$—$CH_2$—$C(CH_3)_2$—$CH_2$—$CH_2$—, and $C_6$-$C_{20}$ (alkyl) phenylene, such as 2-methyl-1,3-phenylene.

Preferably, L is chosen from: -isophorone-; —$(CH_2)_6$—; and 4,4'-methylene biscyclohexylene.

According to one particularly preferred embodiment, the junction group is of formula

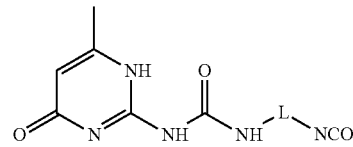

in which L is isophorone.

In one particularly preferred embodiment, the supramolecular polymer of the invention corresponds to the formula:

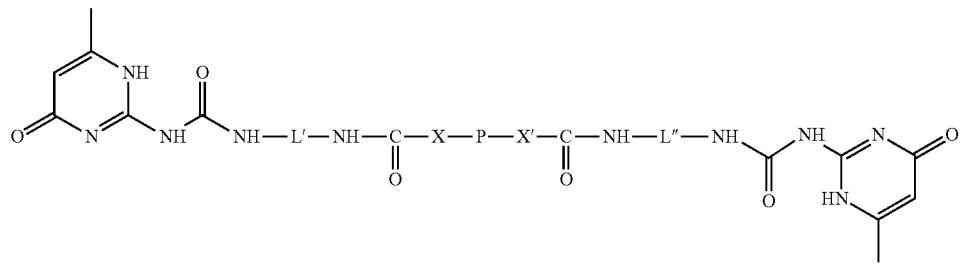

in which:

L' and L" have, independently of each other, the following meaning: a single bond or a saturated or unsaturated $C_{1-20}$ divalent carbon-based group chosen in particular from a linear or branched $C_1$-$C_{20}$ alkylene; a $C_5$-$C_{20}$ (alkyl)cycloalkylene alkylene (preferably cyclohexylene methylene); a $C_{11}$-$C_{20}$ alkylene-biscycloalkylene (preferably alkylene-biscyclohexylene); a $C_6$-$C_{20}$ (alkyl)arylene; and an alkylene-bisarylene (preferably an alkylene-biphenylene);

wherein one or both of L' and L" are possibly substituted with at least one alkyl group and/or possibly comprising 1 to 4 N and/or O heteroatoms, especially in the form of an $NO_2$ substituent;

X and X'=O; and P has the meaning given above for the functionalized polyalkene polymer.

Preferably, L' and L" each independently represent a saturated or unsaturated divalent $C_1$-$C_{20}$ carbon-based group chosen in particular from a linear or branched $C_1$-$C_{20}$ alkylene; a $C_5$-$C_{20}$ (alkyl)cycloalkylene; an alkylene-biscycloalkylene; and a $C_6$-$C_{20}$ (alkyl)arylene. Preferably, L' and L" each independently represent a group chosen from: -isophorone-; —$(CH_2)_2$—; —$(CH_2)_6$—; —$CH_2CH(CH_3)$—$CH_2$—$C(CH_3)_2$—$CH_2$—$CH_2$—; 4,4'-methylene biscyclohexylene; and 2-methyl-1,3-phenylene.

Preferably, L' and L" are identical.

Preferably, L' and L" are each an isophorone group.

Preferably, P is hydrogenated and represents a polyethylene, a polybutylene, a polybutadiene, a polyisoprene, a poly (1,3-pentadiene), a polyisobutylene, or a copolymer thereof, especially a poly(ethylene/butylene).

Preferably, P is a hydrogenated polybutadiene, preferably a hydrogenated 1,2-polybutadiene.

In one particularly preferred embodiment, the supramolecular polymer of the invention corresponds to the formula (I) below:

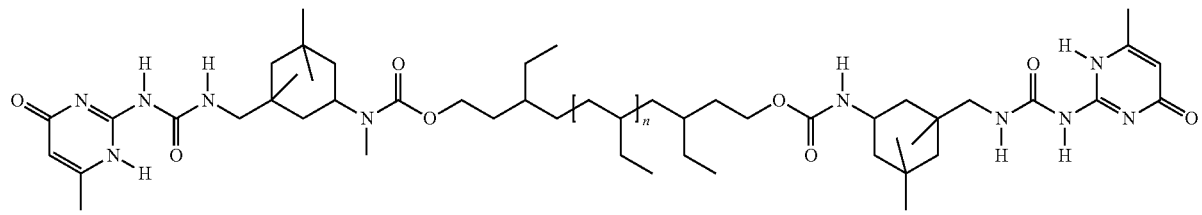

Formula (I)

wherein n can be an integer from 20 to 70; most preferably an integer from 30 to 40.

Preparation Process

The polymer according to the invention may be prepared via the processes usually used by a person skilled in the art, especially for forming a urethane bond between the free OH functions of a polyalkene, and the isocyanate functions borne by the junction group.

By way of non-limiting illustration, a first general preparation process consists in:

optionally ensuring that the polymer to be functionalized does not comprise any residual water;

heating the said polymer comprising at least two reactive OH functions to a temperature that may be between 60° C. and 140° C.; the hydroxyl number of the polymer possibly serving as a reference in order to measure the degree of progress of the reaction;

adding, preferably directly, the ureidopyrimidone junction group bearing the reactive functions, especially isocyanate such as those described in patent WO 2005/042 641; especially such as the junction groups having the CAS numbers 32093-85-9 and 709028-42-2;

optionally stirring the mixture, under a controlled atmosphere, at a temperature of about 90-130° C.; for 1 to 24 hours;

optionally monitoring by infrared spectroscopy the disappearance of the characteristic isocyanate band (between 2500 and 2800 cm$^{-1}$) so as to stop the reaction on total disappearance of the peak, and then allowing the final product to cool to room temperature.

The reaction may also be monitored by assaying the hydroxyl functions; it is also possible to add ethanol in order to ensure the total disappearance of the residual isocyanate functions.

The reaction may be performed in the presence of a solvent, especially methyltetrahydrofuran, tetrahydrofuran, toluene, propylene carbonate or butyl acetate. It is also possible to add a conventional catalyst for forming a urethane bond. An example that may be mentioned is dibutyltin dilaurate. The polymer may finally be washed and dried, or even purified, according to the general knowledge of a person skilled in the art.

According to the second preferred mode of preparation, the reaction may comprise the following steps:

Step (i)

Functionalization of the polymer, which has preferably been dried beforehand, with a diisocyanate according to the reaction scheme:

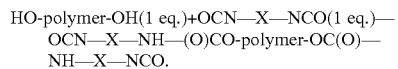

The diisocyanate may optionally be in excess relative to the polymer. This first step may be performed in the presence of a solvent, at a temperature of between 20° C. 100° C. This first step may be followed by a period of stirring under a controlled atmosphere for 1 to 24 hours. The mixture may optionally be heated. The degree of progress of this first step may be monitored by assaying the hydroxyl functions.

Step (ii)

Reaction of the prepolymer obtained above with 6-methylisocytosine of formula:

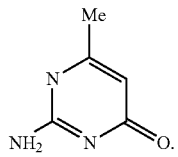

This second step may optionally be performed in the presence of a cosolvent such as toluene, butyl acetate or propylene carbonate. The reaction mixture may be heated to between 80° C. and 140° C. for a time ranging between 1 and 24 hours. The presence of a catalyst, especially dibutyltin dilaurate, may promote the production of the desired final product.

The reaction may be monitored by infrared spectroscopy, by monitoring the disappearance of the characteristic peak of isocyanate between 2200 and 2300 cm$^{-1}$. At the end of the reaction, ethanol may be added to the reaction medium in order to neutralize any residual isocyanate functions. The reaction mixture may be optionally filtered. The polymer may also be stripped directly in a cosmetic solvent.

According to one particular mode, the said supramolecular polymer is dissolved in a hydrocarbon-based oil, which is preferably volatile, in particular isododecane.

Thus, the composition of the invention will comprise at least one hydrocarbon-based oil, which is preferably volatile, in particular at least isododecane, especially provided by the supramolecular polymer solution.

In particular, the supramolecular polymer(s) may be present in a composition according to the invention in an amount ranging from about 1% to about 60% by weight, preferably from about 3% to about 45% by weight, more preferably from about 5% to about 20% by weight, based on the total weight of the composition.

In another particular embodiment of the invention, a makeup composition is in the form of a lipstick and the supramolecular polymer(s) may be present therein in a content ranging from about 1% to about 40% by weight, preferably from about 3% to about 30% by weight, more preferably from about 5% to about 15% by weight, based on the total weight of the composition.

Hyperbranched Polymers

Hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have: an extremely branched structure around a core; successive generations or layers of branching; a layer of end chains.

Hyperbranched polymers are polymers that are highly branched and contain large number of end groups. Hyperbranched polymer usually contains a central core and the growth of the polymer emanates from this central core. The growth of the polymer is made possible by repeating units of single monomers or linear chains added onto the central core. The end unit of the single monomer or linear chain can be functionalized which can become junction points (i.e., linkage points) for further growth of the polymer. The final form of the hyperbranched polymer exhibits a tree-like structure without any symmetry or regularity.

The synthesis of hyperbranched polymer can be produced by single monomer methodology (SMM) or double monomer methodology (DMM) (Gao and Yan, 2004). For SMM, polymerization involves an $AB_x$, AB* or a latent $AB_x$ monomer through generally four different types of reaction mechanism: polycondensation of $AB_x$ monomers, self-condensing vinyl polymerization (SCVP), self-condensation ring opening polymerization (SCROP) and proton transfer polymerization (PTP). For DMM, a direct polymerization is possible with two types of monomers or monomer pairs, the most notable being the polymerization of "$A_2+B_n$, n≥2", and the couple-monomer methodology (CMM) has also been used.

There are several ways to characterize the topology of a hyperbranched polymer, such as, by its degree of branching and the Wiener index. The degree of branching is defined as B=2D/(2D+L) where D is the number of fully branched units and L is the number of partially reacted units (Holter et al., 1997). For a completely linear polymer, B=0 and for a fully branched hyperbranched polymer B=1. The Wiener index states the sum of paths or branches between all pairs of non-hydrogen atoms in a molecule (Wiener, 1947). It is defined as $$W = \frac{1}{2}\sum_{j=1}^{Ns}\sum_{i=1}^{Ns} d_{ij}$$

where N is the degree of polymerization and $d_{ij}$ is the number of bonds separating site i and j of the molecule. For two polymers with equal number of molecular weight, the linear polymer will have a smaller Wiener number than the hyperbranched polymer.

An end group can be reacted with the hyperbranched polymer to obtain a particular functionality on the ends of chains.

Hyperbranched Functional Polymers

"Hyperbranched functional polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point (i.e., linkage point) between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points (i.e., linkage points) between at least three polymeric branches, for example n polymeric branches (wherein n=3 or more), of which n–1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

Suitable hyperbranched functional polymers include, but are not limited to, hyperbranched polyols and hyperbranched polyacids.

The at least one hyperbranched functional polymer may be present in the composition of the present invention in an amount ranging from about 0.1 to about 30% by weight, more preferably from about 1 to about 20% by weight, most preferably from about 2 to about 10% by weight, relative to the total weight of the composition. In certain preferred embodiments of the present invention (e.g., where the composition is in the form of a lipstick and the amount of supramolecular polymer is from about 5 to about 15% by weight based on the total weight of the composition), the at least one hyperbranched functional polymer may be present in the composition of the present invention in an amount ranging from 7.5 to about 10% by weight relative to the total weight of the composition.

Hyperbranched Polyol Compound

According to the present invention, compositions comprising at least one hyperbranched polyol compound are provided.

The at least one hyperbranched polyol compound of the present invention has at least two hydroxyl groups. Preferably, the hyperbranched polyol has a hydroxyl number of at least 15, more preferably of at least 50, more preferably of at least 100, and more preferably of at least about 150. "Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample.

According to preferred embodiments, the at least one hyperbranched polyol has a hydroxyl number between 50 and 250, preferably between 75 and 225, preferably between 100 and 200, preferably between 125 and 175, including all ranges and subranges therebetween such as 90 to 150.

In accordance with the present invention, "hyperbranched polyol" refers to dendrimers, hyperbranched macromolecules and other dendron-based architectures.

Hyperbranched polyols can generally be described as three-dimensional highly branched molecules having a tree-like structure. They are characterized by a great number of end groups, at least two of which are hydroxyl groups. The dendritic or "tree-like" structure preferably shows irregular non-symmetric branching from a central multifunctional core molecule leading to a compact globular or quasi-globular structure with a large number of end groups per molecule. Suitable examples of hyperbranched polyols can be found in U.S. Pat. No. 7,423,104, and U.S. patent applications 2008/0207871 and 2008/0286152, the entire contents of all of which are hereby incorporated by reference.

Other suitable examples include alcohol functional olefinic polymers such as those available from New Phase Technologies. For example, olefinic polymers can include a functionalized polyalphaolefin comprising the reaction product of admixing an alpha-olefin monomer having at least 10 carbon atoms and an unsaturated functionalizing compound. Non-functionalized olefins that may be used in accordance with the present invention include, but are not limited to, 1-decene, 1-dodecene, 1-tetradecene, 1-hexadecene, 1-octadecene, 1-eicosene, as well as such commercial mixtures sold as alpha-olefins including those having mainly C10-C13, C20-C24 chain lengths, C24-C28 chain lengths and C30 and higher chain lengths.

Unsaturated functionalizing compounds useful with the present invention are chosen from alcohols, including olefinic alcohols such as allyl alcohol, 9-decen-1-ol, 10-undecylenyl alcohol, oleyl alcohol, and erucyl alcohol. The molar ratio of alpha-olefin monomer to unsaturated functionalizing compound can range from about 20:1 to 1:20 such as from about 10:1 to 1:10 or such as from about 8:1 to 1:2.

After the polymerization, the alcohol functional olefinic polymers preferably have molecular weights, determined using gel permeation chromatography procedure and a polystyrene standard, of from about 200 daltons to about 150,000 daltons, such as from about 400 daltons to about 80,000 daltons or such as from about 600 daltons to about 6,000 daltons.

According to certain embodiments, the alcohol functional olefinic polymer has a dynamic viscosity ranging from 0.1 Pa·s to 100 Pa·s, such as from 0.1 Pa·s to 50 Pa·s, or such as from 0.1 Pa·s to 10 Pa·s at room temperature.

According to particularly preferred embodiments of the present invention, the at least one hyperbranched polyol compound comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are, for example, acyclic, cyclic, polycyclic, linear, branched, substituted, unsubstituted, functionalized or non-functionalized. For example, suitable monomers include ethylene, propylene, 1-butene, 2-butene, 3-methyl-1-butene, and isobutylene.

Suitable silicone groups for inclusion into the interior chain include, but are not limited to, M, D, T, and/or Q groups in accordance with commonly used silicon-related terminology (M=monovalent; D=divalent; T=trivalent; and Q=quadvalent). Particularly preferred monomers are "D" groups such as dimethicone or substituted dimethicone groups. Such groups can help form, for example, suitable dimethicone copolyols in accordance with the present invention.

A preferred structure of the at least one hyperbranched polyol of the present invention is as follows:

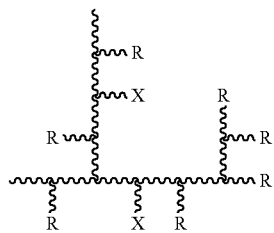

Where X corresponds to hydroxyl functionality and R corresponds to a methyl group or an alkyl group preferably containing 2-30 atoms.

According to preferred embodiments, the at least one hyperbranched polyol compound has a molecular weight (Mw) between about 1,000 and about 25,000, preferably between about 2,000 and about 22,000, preferably between about 3,000 and about 20,000, including all ranges and subranges therebetween such as about 4000 to about 5500.

According to preferred embodiments, the at least one hyperbranched polyol compound has a viscosity at 90° F. of between 0.01 Pa·s and 10 Pa·s, such as between 0.02 and 7 Pa·s, and such as between 0.03 and 6 Pa·s, including all ranges and subranges therebetween. The viscosity is determined using Brookfield viscometer at 90° F. by ASTMD-3236MOD method.

A particularly preferred at least one hyperbranched polyol compound for use in the present invention is C20-C24 olefin/oleyl alcohol copolymer, commercially available from New Phase Technologies under the trade name Performa V™-6175.

The at least one hyperbranched polyol compound may be present in the composition of the present invention in an amount ranging from about 1 to about 30% by weight, more preferably from about 5 to about 25% by weight, most preferably from about 10 to about 20% by weight, relative to the total weight of the composition.

Hyperbranched Polyacid

According to the present invention, compositions comprising at least one hyperbranched polyacid compound are provided. The aforementioned "hyperbranched polyol" refers to the hyperbranched functional polymer wherein the functional groups are substituted with hydroxyl groups. Similar definition applies to the term "hyperbranched polyacid" wherein the functional groups of the hyperbranched functional polymer are substituted with carboxylic acid groups.

The at least one hyperbranched polyacid compound of the present invention has at least two carboxyl groups. Preferably, the hyperbranched polyacid has a carboxyl number of at least 3, more preferably of at least 10, more preferably of at least 50, and more preferably of at least about 150.

According to preferred embodiments, the at least one hyperbranched polyacid has a carboxyl number between 50 and 250, preferably between 75 and 225, preferably between 100 and 200, preferably between 125 and 175, including all ranges and subranges there between such as 90 to 150.

Suitable examples of hyperbranched polyacids can be found in U.S. Pat. No. 7,582,719, and EP1367080, the entire contents of all of which are hereby incorporated by reference.

Unsaturated functionalizing compounds useful with the present invention include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

A particularly preferred acid functional olefinic polymer is C30+ olefin/undecylenic acid copolymer available from New Phase Technologies under trade name Performa V™-6112.

According to preferred embodiments, the at least one hyperbranched acid compound has a molecular weight (Mw) between about 500 and about 25,000, preferably between about 800 and about 10000, preferably between about 1000 and about 8000, including all ranges and subranges there between such as about 1000 to about 6000.

According to preferred embodiments, the at least one hyperbranched polyacid compound has a viscosity at 210° F. of between 0.01 Pa·s and 10 Pa·s, such as between 0.02 and 7 Pa·s, and such as between 0.03 and 6 Pa·s, including all ranges and subranges there between. The viscosity is determined using Brookfield viscometer at 210° F. by ASTMD-3236MOD method.

According to preferred embodiments, the at least one hyperbranched acid compound has an acid number between about 20 and about 400 mg/KOH, more preferably between about 30 and about 300 mg/KOH, and even more preferably between about 50 and about 100 mg/KOH.

The at least one hyperbranched polyacid compound is present in the composition of the present invention in an amount ranging from about 0.1 to about 20% by weight, more preferably from about 0.2 to about 10% by weight, most preferably from about 2 to about 10% by weight, relative to the total weight of the composition. In certain preferred embodiments of the present invention (e.g., where the composition is in the form of a lipstick and the amount of supramolecular polymer is from about 5 to about 15% by weight based on the total weight of the composition), the at least one hyperbranched polyacid may be present in the composition of the present invention in an amount ranging from 7.5 to about 10% by weight relative to the total weight of the composition.

Fatty Phase

A composition according to the invention further comprises a fatty phase. This fatty phase may comprise oils, waxes and/or pasty compounds and/or silicone compounds as defined below.

The fatty phase ranges from 1% to 97% by weight, especially 5% to 95% by weight or even 10% to 90% by weight, relative to the total weight of the composition.

Thus, a composition according to the invention may advantageously comprise one or more oils, which may be chosen especially from hydrocarbon-based oils and fluoro oils, and mixtures thereof. The oils may be of animal, plant, mineral or synthetic origin.

The term "oil" means a water-immiscible non-aqueous compound that is liquid at room temperature (25° C.) and at atmospheric pressure (760 mmHg).

The oils may be volatile or non-volatile.

For the purposes of the invention, the term "volatile oil" means any oil that is capable of evaporating on contact with keratin materials in less than one hour, at room temperature and atmospheric pressure. Volatile oils preferably have a non-zero vapour pressure, at room temperature and atmospheric pressure, ranging from 0.13 Pa to 40,000 Pa, in particular from 1.3 Pa to 13,000 Pa and more particularly from 1.3 Pa to 1,300 Pa.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Non-volatile oils that may especially be mentioned include:
- hydrocarbon-based oils of animal origin,
- hydrocarbon-based oils of plant origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_4$ to $C_{36}$ and especially from $C_{is}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel,
- synthetic ethers containing from 10 to 40 carbon atoms;
- synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate, polyol esters and pentaerythritol esters, for instance dipentaerythrityl tetrahydroxystearate/tetraisostearate, esters of diol dimers and of diacid dimers, copolymers of diol dimer and of diacid dimer and esters thereof, such as dilinoleyl diol dimer/dilinoleic dimer copolymers, and esters thereof, copolymers of polyols and of diacid dimers, and esters thereof, fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol, $C_{12}$-$C_{22}$ higher fatty acids, such as oleic acid, linoleic acid and linolenic acid, and mixtures thereof;

dialkyl carbonates, the two alkyl chains possibly being identical or different, such as dicaprylyl carbonate;

oils with a molar mass of between about 400 and about 10,000 g/mol, in particular about 650 to about 10,000 g/mol, in particular from about 750 to about 7,500 g/mol and more particularly ranging from about 1,000 to about 5,000 g/mol; mention may be made especially, alone or as a mixture, of (i) lipophilic polymers such as polybutylenes, polyisobutylenes, for example hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly(2-glyceryl)tetraisostearate or pentaerythrityl 2-tetradecyltetradecanoate; (vi) diol dimer esters and polyesters, such as esters of diol dimer and of fatty acid, and esters of diol dimer and of diacid.

In particular, one or more oils according to the invention may be present in a composition according to the invention in a content ranging from 1% to 90% by weight, preferably ranging from 2% to 75% by weight or even from 3% to 60% by weight relative to the total weight of the composition.

It is understood that the above-described weight percentage of oil takes into account the weight of oil used for the formulation of the associated supramolecular polymer, if present.

Silicone Oils

For the purposes of the present invention, the term "silicone oil" means an oil comprising at least one silicon atom, and especially at least one Si—O group.

In particular, the volatile or non-volatile silicone oils that may be used in the invention preferably have a viscosity at 25° C. of less than 800,000 cSt, preferably less than or equal to 600,000 cSt and preferably less than or equal to 500,000 cSt. The viscosity of these silicone oils may be measured according to standard ASTM D-445.

The silicone oils that may be used according to the invention may be volatile or non-volatile or mixtures of volatile and non-volatile silicone oils.

Thus, a composition according to the invention or under consideration according to a process of the invention may contain a mixture of volatile and non-volatile silicone oils.

In a preferred embodiment, the term "volatile silicone oil" means an oil that can evaporate on contact with the skin in less than one hour, at room temperature (25° C.) and atmospheric pressure. The volatile silicone oil is a volatile cosmetic oil, which is liquid at room temperature, especially having a non-zero vapour pressure, at room temperature and atmospheric pressure, in particular having a vapour pressure ranging from 0.13 Pa to 40,000 Pa ($10^{-3}$ to 300 mmHg), preferably ranging from 1.3 Pa to 13,000 Pa (0.01 to 100 mmHg) and preferentially ranging from 1.3 Pa to 1,300 Pa (0.1 to 10 mmHg).

The term "non-volatile silicone oil" means an oil whose vapour pressure at room temperature and atmospheric pressure is non-zero and less than 0.02 mmHg (2.66 Pa) and better still less than $10^{-3}$ mmHg (0.13 Pa).

Volatile Silicone Oils

In one embodiment of the present invention, compositions according to the invention comprise at least one volatile silicone oil.

The volatile silicone oils that may be used in the invention may be chosen from silicone oils especially having a viscosity ≤8 centistokes (cSt) ($8\times10^{-6}$ m$^2$/s).

Furthermore, the volatile silicone oil that may be used in the invention may preferably be chosen from silicone oils with a flash point ranging from 40° C. to 102° C., preferably with a flash point of greater than 55° C. and less than or equal to 95° C., and preferentially ranging from 65° C. to 95° C. Volatile silicone oils that may be mentioned include: volatile linear or cyclic silicone oils, especially those with a viscosity ≤8 centistokes (cSt) ($8\times10^{-6}$ m$^2$/s at 25° C.), and especially containing from 2 to 10 silicon atoms and in particular from 2 to 7 silicon atoms, these silicones optionally comprising alkyl or alkoxy groups containing from 1 to 10 carbon atoms.

More particularly, the volatile silicone oils are non-cyclic and are chosen in particular from:

(a) the non-cyclic linear silicones of formula (D):

$$R_3SiO\text{—}(R_2SiO)_n\text{—}SiR_3 \quad (D)$$

in which R, which may be identical or different, denotes:

a saturated or unsaturated hydrocarbon-based radical, containing from 1 to 10 carbon atoms and preferably from 1 to 6 carbon atoms, optionally substituted with one or more fluorine atoms or with one or more hydroxyl groups, or a hydroxyl group, one of the radicals R possibly being a phenyl group, n is an integer ranging from 0 to 8, preferably ranging from 2 to 6 and better still ranging from 3 to 5, further wherein none of the R groups in the silicone compound of formula (D) contain more than 15 carbon atoms;

(b) the branched silicones of formula (E) or (F) below:

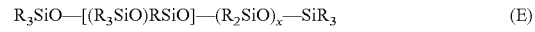

$$R_3SiO\text{—}[(R_3SiO)RSiO]\text{—}(R_2SiO)_x\text{—}SiR_3 \quad (E)$$

$$[R_3SiO]4Si \quad (F)$$

in which R, which may be identical or different, denotes:
a saturated or unsaturated hydrocarbon-based radical, containing from 1 to 10 carbon atoms, optionally substituted with one or more fluorine atoms or with one or more hydroxyl groups, or a hydroxyl group, one of the radicals R possibly being a phenyl group, x is an integer ranging from 0 to 8, further wherein none of the R groups in the silicone compound of formula (E) or (F) contain more than 15 carbon atoms.

Preferably, for the compounds of formulae (D), (E) and (F), the ratio between the number of carbon atoms and the number of silicon atoms is between 2.25 and 4.33.

The silicones of formulae (D) to (F) may be prepared according to the known processes for synthesizing silicone compounds.

Among the silicones of formula (D) that may be mentioned are:

the following disiloxanes: hexamethyldisiloxane (surface tension=15.9 mN/m), sold especially under the name DC 200 Fluid 0.65 cSt by the company Dow Corning, 1,3-di-tert-butyl-1,1,3,3-tetramethyldisiloxane; 1,3-dipropyl-1,1,3,3-tetramethyldisiloxane; heptylpentamethyldisiloxane; 1,1,1-triethyl-3,3,3-trimethyldisiloxane; hexaethyldisiloxane; 1,1,3,3-tetramethyl-1,3-bis(2-methylpropyl)disiloxane; pentamethyloctyldisiloxane; 1,1,1-trimethyl-3,3,3-tris(1-methylethyl)disiloxane; 1-butyl-3-ethyl-1,1,3-trimethyl-3-propyldisiloxane; pentamethylpentyldisiloxane; 1-butyl-1,1,3,3-tetramethyl-3-(1-methylethyl)disiloxane; 1,1,3,3-tetramethyl-1,3-bis(1-methylpropyl)disiloxane; 1,1,3-triethyl-1,3,3-tripropyldisiloxane; 3,3-dimethylbutyl)pentamethyldisiloxane; (3-methylbutyl)pentamethyldisiloxane; (3-methylpentyl)pentamethyldisiloxane; 1,1,1-triethyl-3,3-dimethyl-3-propyldisiloxane; 1-(1,1-dimethylethyl)-1,1,3,3,3-pentamethyldisiloxane; 1,1,1-trimethyl-3,3,3-tripropyldisiloxane; 1,3-dimethyl-1,1,3,3-tetrakis(1-methylethyl)disiloxane; 1,1-dibutyl-1,3,3,3-tetramethyldisiloxane; 1,1,3,3-tetramethyl-1,3-bis(1-methylethyl)disiloxane; 1,1,3-tetramethyl-3,3-bis(1-methylethyl)disiloxane; 1,1,3-tetramethyl-3,3-dipropyldisiloxane; 1,1,3,3-tetramethyl-1,3-bis(3-methylbutyl)disiloxane; butylpentamethyldisiloxane; pentaethylmethyldisiloxane; 1,1,3,3-tetramethyl-1,3-dipentyldisiloxane; 1,3-dimethyl-1,1,3,3-tetrapropyldisiloxane; 1,1,1,3-tetraethyl-3,3-dimethyldisiloxane; 1,1,1-triethyl-3,3,3-tripropyldisiloxane; 1,3-dibutyl-1,1,3,3-tetramethyldisiloxane and hexylpentamethyldisiloxane;

the following trisiloxanes: octamethyltrisiloxane (surface tension=17.4 mN/m), sold especially under the name DC 200 Fluid 1 cSt by the company Dow Corning, 3-pentyl-1,1,1,3,5,5,5-heptamethyltrisiloxane; 1-hexyl-1,1,3,3,5,5,5-heptamethyltrisiloxane; 1,1,1,3,3,5,5-heptamethyl-5-octyltrisiloxane; 1,1,1,3,5,5,5-heptamethyl-3-octyltrisiloxane, sold especially under the name Silsoft 034 by the company OSI; 1,1,1,3,5,5,5-heptamethyl-3-hexyltrisiloxane (surface tension=20.5 mN/m), sold especially under the name DC 2-1731 by the company Dow Corning; 1,1,3,3,5,5-hexamethyl-1,5-dipropyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 1,1,1,3,3,5,5-hexamethyl-1,5-bis(1-methylpropyl)trisiloxane; 1,5-bis(1,1-dimethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5,5-pentamethyltrisiloxane; heptamethyltrisiloxane; 3-tert-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3,-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane and 1-ethyl-1,1,3,3,5,5,5-heptamethyltrisiloxane;

the following tetrasiloxanes: decamethyltetrasiloxane (surface tension=18 mN/m), sold especially under the name DC 200 Fluid 1.5 cSt by the company Dow Corning; 1,1,3,3,5,5,7,7-octamethyl-1,7-dipropyltetrasiloxane; 1,1,1,3,3,5,7,7,7-nonamethyl-5-(1-methylethyl)tetrasiloxane; 1-butyl-1,1,3,3,5,5,7,7,7-nonamethyltetrasiloxane; 3,5-diethyl-1,1,1,3,5,7,7,7-octamethyltetrasiloxane; 1,3,5,7-tetraethyl-1,1,3,5,7,7-hexamethyltetrasiloxane; 3,3,5,5-tetraethyl-1,1,1,7,7,7-hexamethyltetrasiloxane; 1,1,1,3,3,5,5,7,7-nonamethyl-7-phenyltetrasiloxane; 3,3-diethyl-1,1,1,5,5,7,7,7-octamethyltetrasiloxane; and 1,1,1,3,3,5,7,7,7-nonamethyl-5-phenyltetrasiloxane;

the following pentasiloxanes: dodecamethylpentasiloxane (surface tension=18.7 mN/m), sold especially under the name DC 200 Fluid 2 cSt by the company Dow Corning; 1,1,3,3,5,5,7,7,9,9-decamethyl-1,9-dipropylpentasiloxane; 3,3,5,5,7,7-hexaethyl-1,1,1,9,9,9-hexamethylpentasiloxane; 1,1,1,3,3,5,7,7,9,9,9-undecamethyl-5-phenylpentasiloxane; 1-butyl-1,1,3,3,5,5,7,7,9,9,9-undecamethylpentasiloxane; 3,3-diethyl-1,1,1,5,5,7,7,9,9,9-decamethylpentasiloxane; 1,3,5,7,9-pentaethyl-1,1,3,5,7,9,9-heptamethylpentasiloxane; 3,5,7-triethyl-1,1,1,3,5,7,9,9,9-nonamethylpentasiloxane and 1,1,1-triethyl-3,3,5,5,7,7,9,9,9-nonamethylpentasiloxane;

the following hexasiloxanes: 1-butyl-1,1,3,3,5,5,7,7,9,9,11,11,11-tridecamethylhexasiloxane; 3,5,7,9-tetraethyl-1,1,1,3,5,7,9,11,11,11-decamethylhexasiloxane and tetradecamethylhexasiloxane.

hexadecamethylheptasiloxane;
octadecamethyloctasiloxane;
eicosamethylnonasiloxane.

Among the silicones of formula (E) that may be mentioned are:

the following tetrasiloxanes: 2-[3,3,3-trimethyl-1,1-bis[(trimethylsilyl)oxy]disiloxanyl]ethyl; 1,1,1,5,5,5-hexamethyl-3-(2-methylpropyl)-3-[(trimethylsilyl)oxy]trisiloxane; 3-(1,1-dimethylethyl)-1,1,1,5,5,5-hexamethyl-3-[(trimethylsilyl)oxy]trisiloxane; 3-butyl-1,1,1,5,5,5-hexamethyl-3-[(trimethylsilyl)oxy]trisiloxane; 1,1,1,5,5,5-hexamethyl-3-propyl-3-[(trimethylsilyl)oxy]trisiloxane; 3-ethyl-1,1,1,5,5,5-hexamethyl-3-[(trimethylsilyl)oxy]trisiloxane; 1,1,1-triethyl-3,5,5,5-tetramethyl-3-(trimethylsiloxy)trisiloxane; 3-methyl-1,1,1,5,5,5-hexamethyl-3-[trimethylsilyl)oxy]trisiloxane; 3-[(dimethylphenylsilyl)oxy]-1,1,1,3,5,5,5-heptamethyltrisiloxane; 1,1,1,5,5,5-hexamethyl-3-(2-methylpentyl)-3-[(trimethylsilyl)oxy]trisiloxane; 1,1,1,5,5,5-hexamethyl-3-(4-methylpentyl)-3-[(trimethylsilyl)oxy]trisiloxane; 3-hexyl-1,1,1,5,5,5-hexamethyl-3-[(trimethylsilyl)oxy]trisiloxane and 1,1,1,3,5,5,5-heptamethyl-3-[(trimethylsilyl)oxy]trisiloxane;

the following pentasiloxanes: 1,1,1,3,5,5,7,7,7-nonamethyl-3-(trimethylsiloxy)tetrasiloxane and 1,1,1,3,3,7,7,7-octamethyl-5-phenyl-5-[(trimethylsilyl)oxy]tetrasiloxane;

the following hexasiloxane: 1,1,1,3,5,5,7,7,9,9,11,11,11-tridecamethyl-3-[(trimethylsilyl)oxy]hexasiloxane.

Among the silicones of formula (F), mention may be made of:

1,1,1,5,5,5-hexamethyl-3,3-bis(trimethylsiloxy)trisiloxane.

Use may also be made of other volatile silicone oils chosen from:

the following tetrasiloxanes: 2,2,8,8-tetramethyl-5-[(pentamethyldisiloxanyl)methyl]-3,7-dioxa-2,8-disilanonane; 2,2,5,8,8-pentamethyl-5-[(trimethylsilyl)methoxy]-4,6-dioxa-2,5,8-trisilanonane; 1,3-dimethyl-1,3-bis[(trimethylsilyl)methyl]-1,3-disiloxanediol; 3-ethyl-1,1,1,5,5,5-hexamethyl-3-[3-(trimethylsiloxy)propyl]trisiloxane and 1,1,1,5,5,5-hexamethyl-3-phenyl-3-[(trimethylsilyl)oxy]trisiloxane (Dow 556 Fluid);

the following pentasiloxanes: 2,2,7,7,9,9,11,11,16,16-decamethyl-3,8,10,15-tetraoxa-2,7,9,11,16-pentasilaheptadecane and the tetrakis[(trimethylsilyl)methyl]ester of silicic acid;

the following hexasiloxanes: 3,5-diethyl-1,1,1,7,7,7-hexamethyl-3,5-bis[(trimethylsilyl)oxy]tetrasiloxane and 1,1,1,3,5,7,7,7-octamethyl-3,5-bis[(trimethylsilyl)oxy]tetrasiloxane;

the heptasiloxane: 1,1,1,3,7,7,7-heptamethyl-3,5,5-tris[(trimethylsilyl)oxy]tetrasiloxane;

the following octasiloxanes: 1,1,1,3,5,5,9,9,9-nonamethyl-3,7,7-tris[(trimethylsilyl)oxy]pentasiloxane; 1,1,1,3,5,7,9,9,9-nonamethyl-3,5,7-tris[(trimethylsilyl)oxy]pentasiloxane and 1,1,1,7,7,7-hexamethyl-3,3,5,5-tetrakis[(trimethylsilyl)oxy]tetrasiloxane.

Volatile silicone oils that may more particularly be mentioned include decamethylcyclopentasiloxane sold especially under the name DC-245 by the company Dow Corning, dodecamethylcyclohexasiloxane sold especially under the name DC-246 by the company Dow Corning, octamethyltrisiloxane sold especially under the name DC-200 Fluid 1 cSt by the company Dow Corning, decamethyltetrasiloxane sold especially under the name DC-200 Fluid 1.5 cSt by the company Dow Corning and DC-200 Fluid 5 cSt sold by the company Dow Corning, octamethylcyclotetrasiloxane, heptamethylhexyltrisiloxane, heptamethylethyltrisiloxane, heptamethyloctyltrisiloxane and dodecamethylpentasiloxane, and mixtures thereof.

It should be noted that, among the above-mentioned oils, the linear oils prove to be particularly advantageous.

Non-Volatile Silicone Oils

The non-volatile silicone oils that may be used in the invention may be chosen from silicone oils with a viscosity at 25° C. of greater than or equal to 9 centistokes (cSt) ($9 \times 10^{-6}$ m$^2$/s) and less than 800,000 cSt, preferably between 50 and 600,000 cSt and preferably between 100 and 500,000 cSt. The viscosity of this silicone oil may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes (i.e., PDMS); alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:

PDMSs comprising alkyl or alkoxy groups, which are pendent and/or at the end of the silicone chain, these groups each containing from 2 to 24 carbon atoms, PDMSs comprising aliphatic groups, or functional groups such as hydroxyl, thiol and/or amine groups, polyalkylmethylsiloxanes optionally substituted with a fluorinated group, such as polymethyltrifluoropropyldimethylsiloxanes, polyalkylmethylsiloxanes substituted with functional groups such as hydroxyl, thiol and/or amine groups, polysiloxanes modified with fatty acids, fatty alcohols or polyoxyalkylenes, and mixtures thereof.

According to one embodiment, a composition according to the invention contains at least one non-phenyl linear silicone oil.

The non-phenyl linear silicone oil may be chosen especially from the silicones of formula:

$$X-\underset{R_2}{\overset{R_1}{\underset{|}{\overset{|}{Si}}}}-O-\left[\underset{R_4}{\overset{R_3}{\underset{|}{\overset{|}{Si}}}}-O\right]_n\left[\underset{R_6}{\overset{R_5}{\underset{|}{\overset{|}{Si}}}}-O\right]_p\underset{R_2}{\overset{R_1}{\underset{|}{\overset{|}{Si}}}}-X$$

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound.

As non-volatile silicone oils that may be used according to the invention, mention may be made of those for which:

the substituents $R_1$ to $R_6$ and X represent a methyl group, and p and n are such that the viscosity is about 500,000 cSt (measured by Brookfield viscometer using ASTMD-445 method), such as the product sold under the name SE30 by the company General Electric, the product sold under the name AK 500,000 by the company Wacker, the product sold under the name Mirasil DM 500,000 by the company Bluestar, and the product sold under the name Dow Corning 200 Fluid 500,000 cSt by the company Dow Corning (viscosity determined by Brookfield viscometer using ASTMD-445 method), the substituents $R_1$ to $R_6$ and X represent a methyl group, and p and n are such that the viscosity is about 60,000 cSt (measured by Brookfield viscometer using ASTMD-445 method), such as the product sold under the name Dow Corning 200 Fluid 60,000 CS by the company Dow Corning, and the product sold under the name Wacker Belsil DM 60,000 by the company Wacker, the substituents $R_1$ to $R_6$ and X represent a methyl group, and p and n are such that the viscosity is about 350 cSt (measured by Brookfield viscometer using ASTMD-445 method), such as the product sold under the name Dow Corning 200 Fluid 350 CS by the company Dow Corning, the substituents $R_1$ to $R_6$ represent a methyl group, the group X represents a hydroxyl group, and n and p are such that the viscosity is about 700 cSt (measured by Brookfield viscometer using ASTMD-445 method), such as the product sold under the name Baysilone Fluid T0.7 by the company Momentive.

According to one embodiment variant, a composition according to the invention contains at least one phenyl silicone oil.

Representative examples of these non-volatile phenyl silicone oils that may be mentioned include those oils of Formulae II to VII described below.

The phenyl silicone oils corresponding to the formula (II):

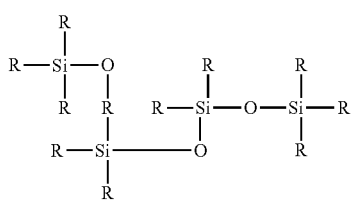

Formula (II)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

The phenyl silicone oils corresponding to the formula (III):

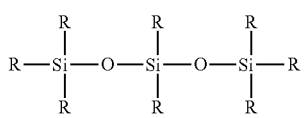

Formula (III)

in which the groups R represent, independently of each other, a methyl or a phenyl, with the proviso that at least one group R represents a phenyl. Preferably, in this formula, the phenyl silicone oil comprises at least three phenyl groups, for example at least four or at least five. Mixtures of these phenyl silicone oils may be used. Examples that may be mentioned include mixtures of triphenyl, tetraphenyl or pentaphenyl organopolysiloxanes.

The phenyl silicone oil corresponding to the formula (IV):

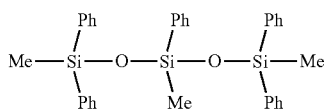

Formula (IV)

in which Me represents methyl, Ph represents phenyl. Such a phenyl silicone oil is especially manufactured by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethyl pentaphenyl trisiloxane). The reference Dow Corning 554 Cosmetic Fluid may also be used.

The phenyl silicone oils corresponding to the formula (V):

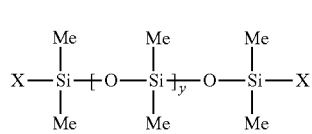

Formula (V)

in which Me represents methyl, y is between 1 and 1,000 and X represents —CH$_2$—CH(CH$_3$)(Ph).

The phenyl silicone oils corresponding to formula (VI) below:

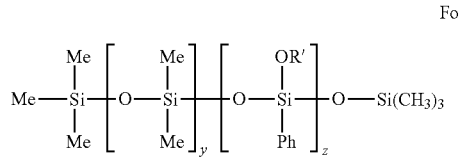

Formula (VI)

in which Me is methyl and Ph is phenyl, OR' represents a group —OSiMe$_3$ and y is 0 or ranges between 1 and 1000, and z ranges between and 1000, such that compound (VI) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid.

The phenyl silicone oils corresponding to the formula (VII):

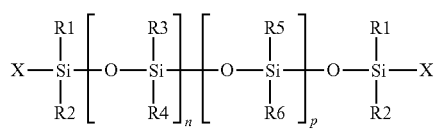

Formula (VII)

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular mass of less than 200,000 g/mol, preferably less than 150,000 g/mol and more preferably less than 100,000 g/mol.

Mixtures of the phenyl silicone oils corresponding to Formulae (II) to (VII) are also useful.

The phenyl silicone oils that are most particularly suitable for use in the invention are those corresponding to formulae (III), (IV) and (VI), especially to formula (IV) and (VI) hereinabove.

More particularly, the phenyl silicone oils are chosen from phenyl trimethicones, phenyl dimethicones, phenyl-trimethylsiloxydiphenylsiloxanes, diphenyl dimethicones, diphenylmethyldiphenyltrisiloxanes and 2-phenylethyl trimethylsiloxysilicates, and mixtures thereof. Preferably, the weight-average molecular weight of the non-volatile phenyl silicone oil according to the invention ranges from 500 to 10,000 g/mol.

Waxes

According to a first embodiment, the composition is free of wax.

According to another embodiment, the composition contains wax.

The term "wax" means a lipophilic compound that is solid at room temperature (25° C.), with a reversible solid/liquid change of state, having a melting point of greater than or equal to 30° C., which may be up to 200° C. The waxes may be chosen from waxes of animal, plant, mineral or synthetic origin, and mixtures thereof. Mention may be made especially of hydrocarbon-based waxes, for instance beeswax, lanolin wax and Chinese insect waxes; rice bran wax, carnauba wax, candelilla wax, ouricury wax, alfalfa wax, berry wax, shellac wax, Japan wax and sumach wax; montan wax, orange wax, lemon wax, microcrystalline waxes, paraffins and ozokerite; polyethylene waxes, the waxes obtained by Fisher-Tropsch synthesis and waxy copolymers, and also esters thereof. Mention may also be made of waxes obtained by catalytic hydrogenation of animal or plant oils containing linear or branched $C_8$-$C_{32}$ fatty chains. Among these, mention may be made especially of hydrogenated sunflower oil, hydrogenated castor oil, hydrogenated coconut oil, hydrogenated lanolin oil and bis(1,1,1-trimethylol propane)tetrastearate. Mention may also be made of silicone waxes and fluoro waxes. The waxes obtained by hydrogenation of castor oil esterified with cetyl alcohol may also be used. According to a preferred embodiment of the invention, the inventive composition contains a polyethylene wax.

The wax may be present in the composition of the present invention in an amount ranging from about 1 to about 25% by weight, more preferably from about 2 to about 20% by weight, most preferably from about 4 to about 15% by weight, relative to the total weight of the composition.

Colorant(s)

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention, including but not limited to, surface treatments with compounds such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45, 170), D&C Red No. 9 (CI 15, 585), D&C Red No. 21 (CI 45, 380), D&C Orange No. 4 (CI 15, 510), D&C Orange No. 5 (CI 45, 370), D&C Red No. 27 (CI 45, 410), D&C Red No. 13 (CI 15,630), D&C Red No. 7 (CI 15, 850), D&C Red No. 6 (CI 15,850), D&C Yellow No. 5 (CI 19, 140), D&C Red No. 36 (CI 12,085), D&C Orange No. 10 (CI 45, 425), D&C Yellow No. 6 (CI 15,985), D&C Red No. 30 (CI 73, 360), D&C Red No. 3 (CI 45, 430) and the dye or lakes based on cochineal carmine (CI 75, 570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

Surfactant(s)

A composition according to the invention may also comprise at least one surfactant, which may be present in a proportion of from about 0.1% to about 10% by weight, especially from about 0.5% to about 8% by weight, or even from about 1% to about 6% by weight relative to the total weight of the composition. The surfactant may be chosen from amphoteric, anionic, cationic and nonionic, preferably nonionic, surfactants. Mention may especially be made, alone or as a mixture, of:

a) nonionic surfactants with an HLB (i.e., hydrophilic-lipophilic balance) of less than 8 at 25° C., optionally combined with one or more nonionic surfactants with an HLB of greater than 8 at 25° C., as mentioned below, for instance:

saccharide esters and ethers such as sucrose stearates, sucrose cocoate and sorbitan stearate, and mixtures thereof;

fatty acid esters, especially of $C_8$-$C_{24}$ and preferably of $C_{16}$-$C_{22}$ fatty acids, and of polyol, especially of glycerol or sorbitol, such as glyceryl stearate, glyceryl laurate, polyglyceryl-2 stearate, sorbitan tristearate and glyceryl ricinoleate;

lecithins, such as soybean lecithins;

oxyethylenated and/or oxypropylenated ethers (which may comprise 1 to 150 oxyethylene and/or oxypropylene groups) of fatty alcohols (especially of $C_8$-$C_{24}$ and preferably $C_{12}$-$C_{18}$ fatty alcohols) such as stearyl alcohol oxyethylene ether containing two oxyethylene units (CTFA name: Steareth-2);

silicone surfactants, for instance dimethicone copolyols and alkyldimethicone copolyols, for example the mixture of cyclomethicone/dimethicone copolyol sold under the name Q2-3225C® by the company Dow Corning;

b) nonionic surfactants, with an HLB of greater than or equal to 8 at 25° C., for instance:

saccharide esters and ethers such as the mixture of cetyl-stearyl glucoside and of cetyl and stearyl alcohols, for instance Montanov 68 from SEPPIC;

oxyethylenated and/or oxypropylenated glycerol ethers, which may comprise 1 to 150 oxyethylene and/or oxypropylene units;

oxyethylenated and/or oxypropylenated ethers (which may comprise from 1 to 150 oxyethylene and/or oxypropylene units) of fatty alcohols, especially of $C_8$-$C_{24}$ and preferably of $C_{12}$-$C_{18}$ fatty alcohols, such as stearyl alcohol oxyethylene ether containing 20 oxyethylene units (CTFA name: Steareth-20), cetearyl alcohol oxyethylene ether containing 30 oxyethylene units (Ceteareth-30) and the oxyethylene ether of the mixture of $C_{12}$-$C_{15}$ fatty alcohols comprising seven oxyethylene units ($C_{12-15}$ Pareth-7);

esters of a fatty acid, especially of $C_8$-$C_{24}$ and preferably of $C_{16}$-$C_{22}$ fatty acids, and of polyethylene glycol (or PEG) (which may comprise 1 to 150 oxyethylene units), such as PEG-50 stearate and PEG-40 monostearate;

esters of a fatty acid, especially of $C_6$-$C_{24}$ and preferably of $C_{16}$-$C_{22}$ fatty acids, and of oxyethylenated and/or oxypropylenated glycerol ethers (which may comprise from 1 to 150 oxyethylene and/or oxypropylene units), for instance glyceryl monostearate polyoxyethylenated with 200 oxyethylene units; glyceryl stearate polyoxyethylenated with 30 oxyethylene units, glyceryl oleate polyoxyethylenated with 30 oxyethylene units, glyceryl cocoate polyoxyethylenated with 30 oxyethylene units, glyceryl isostearate polyoxyethylenated with 30 oxyethylene units and glyceryl laurate polyoxyethylenated with 30 oxyethylene units;

esters of a fatty acid, especially of $C_8$-$C_{24}$ and preferably of $C_{16}$-$C_{22}$ fatty acids, and of oxyethylenated and/or oxypropylenated sorbitol ethers (which may comprise from 1 to 150 oxyethylene and/or oxypropylene units), for instance polysorbate 20 and polysorbate 60;

dimethicone copolyol, especially the product sold under the name Q2-5220® from Dow Corning;

dimethicone copolyol benzoate, such as the products sold under the names Finsolv SLB 101® and 201® from Finetex;

copolymers of propylene oxide and of ethylene oxide, also known as EO/PO polycondensates, which are copolymers formed from polyethylene glycol and polypropylene glycol blocks, for instance polyethylene glycol/polypropylene glycol/polyethylene glycol triblock polycondensates.

c) anionic surfactants such as:

salts of $C_{16}$-$C_{30}$ fatty acids, especially amine salts, such as triethanolamine stearate or 2-amino-2-methylpropane-1,3-diol stearate;

polyoxyethylenated fatty acid salts, especially animated salts or salts of alkali metals, and mixtures thereof;

phosphoric esters and salts thereof, such as DEA oleth-10 phosphate (Crodafos N 10N from the company Croda) or monopotassium monocetyl phosphate;

sulfosuccinates such as disodium PEG-5 citrate lauryl sulfosuccinate and disodium ricinoleamido MEA sulfosuccinate;

alkyl ether sulfates such as sodium lauryl ether sulfate;

isethionates;

acylglutamates such as disodium hydrogenated tallow glutamate (Amisoft HS21 R® from Ajinomoto) and sodium stearoyl glutamate (Amisoft HS11 PF® from Ajinomoto);

soybean derivatives, for instance potassium soyate;

citrates, for instance glyceryl stearate citrate;

proline derivatives, for instance sodium palmitoyl proline or the mixture of sodium palmitoyl sarcosinate, magnesium palmitoyl glutamate, palmitic acid and palmitoyl proline (Sepifeel One from SEPPIC);

lactylates, for instance sodium stearoyl lactylate;

sarcosinates, for instance sodium palmitoyl sarcosinate or the 75/25 mixture of stearoyl sarcosine and myristoyl sarcosine;

sulfonates, for instance sodium $C_{14-17}$ alkyl-sec-sulfonate;

glycinates, for instance sodium cocoyl glycinate.

d) cationic surfactants such as:

alkylimidazolidiniums such as isostearylethylimidonium ethosulfate, ammonium salts such as ($C_{12-30}$ alkyl)tri($C_{1-4}$ alkyl)ammonium halides, for instance N,N,N-trimethyl-1-docosanaminium chloride (or behentrimonium chloride);

e) amphoteric surfactants, for instance N-acylamino acids, such as N-alkylaminoacetates and disodium cocoamphodiacetate, and amine oxides such as stearamine oxide.

Additive(s)

A makeup and/or care composition according to the invention may also comprise at least one agent usually used in cosmetics, chosen, for example, from: reducing agents; thickeners; film-forming agents that are especially hydrophobic, or are softeners, antifoams, moisturizers, or UV-screening agents; ceramides; cosmetic active agents; peptizers; fragrances; proteins; vitamins; propellants; hydrophilic or lipophilic, film-forming or non-film-forming polymers; and lipophilic or hydrophilic gelling agents. The above additives are generally present in an amount for each of them of between 0.01% and 10% by weight relative to the total weight of the composition. A person skilled in the art will take care to select the constituents of the composition such that the advantageous properties associated with the invention are not, or are not substantially, adversely affected.

Cosmetically Acceptable Medium

The ready-to-use composition according to the disclosure can be in various forms, such as in the form of liquids, creams, gels, lotions or paste.

The ready-to-use composition can comprise other compounds constituting the cosmetically acceptable medium. This cosmetically acceptable medium comprises water or a mixture of water and at least one cosmetically acceptable organic solvent.

As examples of cosmetically acceptable organic solvents, non-limiting mentions can be made of alcohols such as ethyl alcohol, isopropyl alcohol, benzyl alcohol and phenylethyl alcohol, or glycols or glycol ethers such as, for example, ethylene glycol, propylene glycol, butylene glycol, hexylene glycol or dipropylene glycol, or ethers thereof such as, for example, monomethyl, monoethyl and monobutyl ethers of ethylene glycol or propylene glycol, such as, for example, monomethyl ethers of propylene glycol, butylene glycol, hexylene glycol or dipropylene glycol, as well as alkyl ethers of diethylene glycol, for example monoethyl ether or monobutyl ether of diethylene glycol.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

EXAMPLES

| INCI US | Comparative Example 1 | Example 1 | Example 2 | Example 3 |
|---|---|---|---|---|
| Lip Compositions | | | | |
| C30 + Olefin/Undecylenic Acid Copolymer (Performa V ™-6112) | 0 | 7 | 7.5 | 9 |
| Supramolecular Polymer of Formula (I) (n = 30-40) | 12.5 | 12.5 | 10 | 10 |
| Red 7 Pigment | 3 | 3 | 3 | 3 |
| Isododecane | QS | QS | QS | QS |

All numerical values in the above Table are weight percent active.

Procedures:

All materials were mixed with moderate agitation at 80 degrees Celsius until all waxes have melted and contents looked uniform. The mixture was then cooled to room temperature while mixing before pouring to suitable size containers for future testing.

The formulation examples above were tested on forearm for olive oil rub test and sensorial tack test upon application.

Evaluation Procedures:

Rub Test on Forearm

Three subjects evaluated the formulations of Comparative Example 1 and Examples 1-3 on the inner forearm on the same day. Each formulation was applied with a lip gloss applicator for 5 strokes and allowed to dry for 10 minutes on forearm and then a drop of olive oil was added to each patch of test area and allowed to rest for 5 minutes before rubbing with Kimwipe 5 times to measure color transfer. Then a visual evaluation score was given to each Kimwipe with a range from 0 to 5 where 0 represents no transfer of color and is desirable and 5 represents all color removal by rubbing and is undesirable.

Sensorial Tack Test

About 20 mg of each of the formulations of Comparative Example 1 and Examples 1-3 were applied onto an aluminium pan surface and allowed to dry for 8 hours at ambient temperature and conditions. Then about 0.3 ml of olive oil was applied onto the color patch surface and allowed to rest for 5 minutes. Afterward, the olive oil was removed with Kimwipe and the color patch surface is tested for sensorial tack test with the same evaluator. The evaluator would apply a compression force with his or her finger on the color patch surface and a score was given to the tack profile of the surface from a range of 0 to 5 where 5 represents most tack and is undesirable and 0 represents no tack and is highly desirable.

| Evaluation Test Method | Comparative Example 1 | Example 1 | Example 2 | Example 3 |
|---|---|---|---|---|
| Rub Test on Forearm | 1 | 4 | 3 | 2 |
| Tack test | 5 | 3 | 2 | 1 |

The results above show that, the inventive formulations of Examples 1-3, which contained a hyperbranched functional polymer, significantly reduced the tackiness disadvantages of the supramolecular polymer. In addition, the formulations of Examples 2 and 3 also provided good wear properties of the lip composition (e.g., good oil resistance upon mechanical stress). The formulations of Examples 2 and 3 are preferred in that they display not only the desired reduction in tackiness but also good wear properties.

It is to be understood that the foregoing describes preferred embodiments of the invention and that modifications may be made therein without departing from the spirit or scope of the invention as set forth in the claims.

What is claimed is:

1. A cosmetic composition for making up and/or enhancing the appearance of keratinous substrates comprising, in a cosmetically acceptable medium:
    a) at least one supramolecular polymer,
    b) at least one detackifying ingredient which is a hyperbranched functional polymer,
    c) at least one fatty phase;
    d) optionally, at least one wax; and
    e) optionally, at least one colorant,
wherein the supramolecular polymer is based on functionalized polyalkene polymer of formula HO—P—OH in which P represents a homopolymer or a copolymer that may be obtained by polymerization of one or more linear or cyclic polyunsaturated $C_2$-$C_{10}$ alkenes, further wherein said one or more linear or cyclic polyunsaturated $C_2$-$C_{10}$ alkenes may be branched, further wherein said supramolecular polymer may be derived from the reaction of said functionalized polyalkene polymer with at least one junction group functionalized with at least one reactive group capable of reacting with the reactive group(s) of the functionalized polyalkene polymer, further wherein said junction group is capable of forming at least 3 hydrogen bonds.

2. The composition according to claim 1, wherein the functionalized polyalkene polymer of formula HO—P—OH is hydrogenated.

3. The composition according to claim 1, wherein P represents a homo- or copolymer that may be obtained by polymerization of one or more linear or branched $C_2$-$C_4$ diunsaturated alkenes.

4. The composition according to claim 1, wherein P is chosen from a polybutylene, a polybutadiene, a polyisoprene, a poly(1,3-pentadiene) or a polyisobutylene, and copolymers thereof.

5. The composition according to claim 1, wherein P is a poly(ethylene/butylene) copolymer.

6. The composition according to claim 1, wherein the functionalized junction group is of formula:

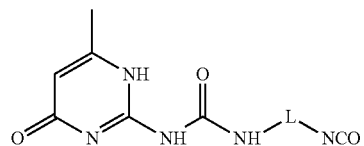

in which L represents a saturated or unsaturated $C_1$-$C_{20}$ divalent carbon-based group.

7. The composition according to claim 1, wherein the supramolecular polymer corresponds to the formula:

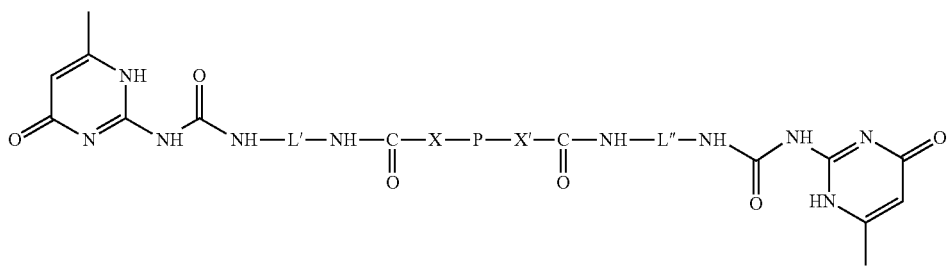

in which:
- L' and L" have, independently of each other, the following meaning: a single bond or a saturated or unsaturated $C_{1-20}$ divalent carbon-based group selected from the group consisting of a linear or branched $C_1$-$C_{20}$ alkylene; a $C_5$-$C_{20}$ (alkyl)cycloalkylene alkylene; a $C_{11}$-$C_{20}$ alkylene-biscycloalkylene; a $C_6$-$C_{20}$ (alkyl)arylene; and an alkylene-bisarylene; wherein one or both of L' and L" are possibly substituted with at least one alkyl group and/or possibly comprising 1 to 4 N and/or O heteroatoms;
- X and X'=O, and P represents a homo- or copolymer that may be obtained by polymerization of one or more linear or branched $C_2$-$C_4$ diunsaturated alkenes.

8. The composition according to claim 7, in which:
L' and L" are both isophorone groups,
X and X'=O, and P represents a polybutylene, a polybutadiene, a polyisoprene, a poly(1,3-pentadiene) or a polyisobutylene, and copolymers thereof.

9. The composition according to claim 1, wherein the supramolecular polymer corresponds to the formula:

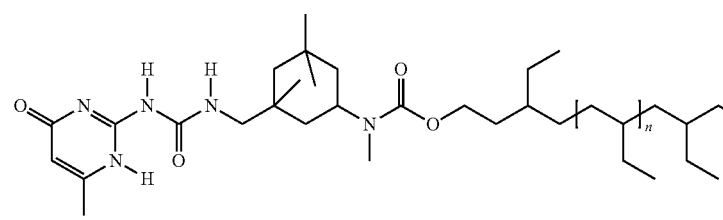

10. The composition according to claim 1, wherein (a) is present in an amount of from about 1 to about 60% by weight, based on the total weight of the composition.

11. The composition according to claim 1, wherein said junction group is capable of forming at least 4 hydrogen bonds.

12. The composition according to claim 6, wherein L is selected from the group consisting of: a linear or branched $C_1$-$C_{20}$ alkylene; a $C_5$-$C_{20}$ (alkyl)cycloalkylene, an alkylene-biscycloalkylene and a $C_6$-$C_{20}$ (alkyl)arylene.

13. The composition according to claim 1, wherein (b) is a hyperbranched polyol.

14. The composition according to claim 1, wherein (b) is a hyperbranched polyacid.

15. The composition according to claim 1, wherein (b) is a C20-C24 olefin/oleyl alcohol copolymer.

16. The composition according to claim 14, wherein the hyperbranched polyacid has at least two carboxyl groups.

17. The composition according to claim 1, wherein (b) is a C30+olefin/undecylenic acid copolymer.

18. The composition according to claim 1, wherein (b) is present in an amount of from about 0.1% to about 30% by weight, based on the total weight of the composition.

19. The composition according to claim 6, wherein L is an isophorone group.

20. The composition according to claim 7, wherein P represents a poly(ethylene/butylene).

21. The composition according to claim 13, wherein the hyperbranched polyol is present in an amount of from about 1% to about 30% by weight, based on the total weight of the composition.

22. The composition according to claim 9, wherein n is an integer from 20 to 70.

23. The composition according to claim 14, wherein the hyperbranched polyacid is present in an amount of from about 0.1% to about 20% by weight, based on the total weight of the composition.

24. The composition according to claim 1, wherein (c) is a silicone oil.

25. The composition according to claim 1, wherein (c) is present in an amount of from about 1% to about 97% by weight, based on the total weight of the composition.

26. The composition according to claim 1, wherein (d) is a polyethylene wax.

27. The composition according to claim 1, wherein (d) is present in an amount of from about 1% to about 25% by weight, based on the total weight of the composition.

28. The composition according to claim 1, wherein the composition is a lip color comprising at least one colorant.

29. The composition according to claim 1, wherein the composition is a lipstick or a lip gloss.

30. A lip color composition comprising:
a) at least one supramolecular polymer having a structure of:

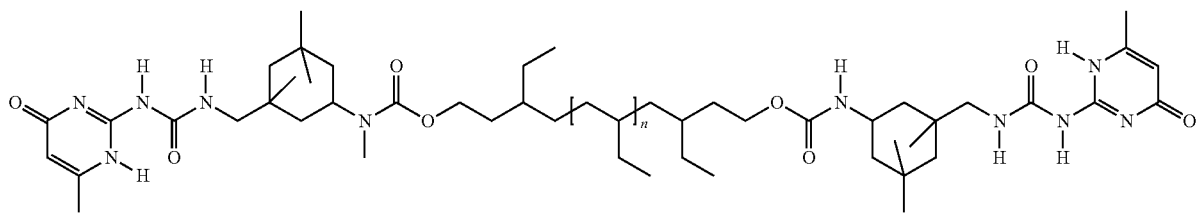

b) a C30+olefin/undecylenic acid copolymer,
c) at least one silicone oil, and
d) at least one colorant.

31. A lip color composition according to claim 30, wherein the at least one supramolecular polymer has the following structure:

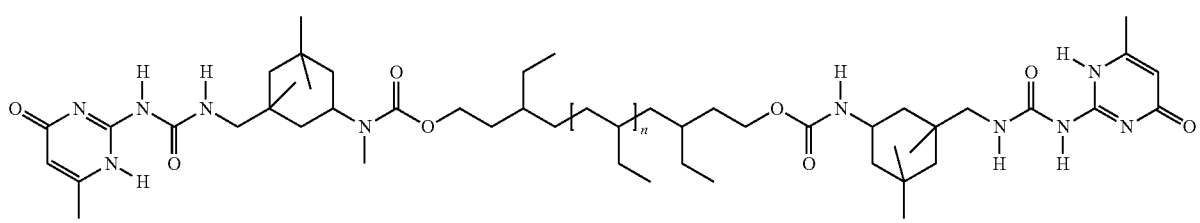

wherein n is an integer from 20 to 70.

32. A method of making up and/or enhancing the appearance of a keratinous substrate comprising applying onto the keratinous substrate a cosmetic composition containing:
 a) at least one supramolecular polymer,
 b) at least one detackifying ingredient which is a hyperbranched functional polymer,
 c) at least one fatty phase;
 d) optionally, at least one wax; and
 e) optionally, at least one colorant,
wherein the supramolecular polymer is based on functionalized polyalkene polymer of formula HO—P—OH in which P represents a homopolymer or a copolymer that may be obtained by polymerization of one or more linear or cyclic polyunsaturated $C_2$-$C_{10}$ alkenes, further wherein said one or more linear or cyclic polyunsaturated $C_2$-$C_{10}$ alkenes may be branched, further wherein said supramolecular polymer may be derived from the reaction of said functionalized polyalkene polymer with at least one junction group functionalized with at least one reactive group capable of reacting with the reactive group(s) of the functionalized polyalkene polymer, further wherein said junction group is capable of forming at least 3 hydrogen bonds.

33. The method according to claim 32, wherein said junction group is capable of forming at least 4 hydrogen bonds.

* * * * *